(12) United States Patent
Fernández De Gatta García et al.

(10) Patent No.: US 8,491,930 B2
(45) Date of Patent: Jul. 23, 2013

(54) PHARMACEUTICAL FORMULATION CONTAINING IBUPROFEN AND CODEINE

(75) Inventors: María Rosario Fernández De Gatta García, Madrid (ES); Eduardo Jáudenes Salazar, Madrid (ES); Tomás Olleros Izard, Madrid (ES)

(73) Assignee: Farmasierra Manufacturing, S.L., Madrid (ES)

( * ) Notice: Subject to any disclaimer, the term of this patent is extended or adjusted under 35 U.S.C. 154(b) by 0 days.

(21) Appl. No.: 12/988,453

(22) PCT Filed: Apr. 23, 2008

(86) PCT No.: PCT/ES2008/070078
§ 371 (c)(1),
(2), (4) Date: Dec. 9, 2010

(87) PCT Pub. No.: WO2009/130342
PCT Pub. Date: Oct. 29, 2009

(65) Prior Publication Data
US 2011/0293716 A1     Dec. 1, 2011

(51) Int. Cl.
*A61K 31/34* (2006.01)
*A61K 31/192* (2006.01)
*A61K 31/195* (2006.01)
*A61K 9/20* (2006.01)
*A01N 43/42* (2006.01)
*A01N 37/44* (2006.01)

(52) U.S. Cl.
USPC ............ 424/465; 514/282; 514/561; 514/568

(58) Field of Classification Search
None
See application file for complete search history.

(56) References Cited

U.S. PATENT DOCUMENTS

| 4,414,198 | A | * | 11/1983 | Michaelson | 424/44 |
| 4,587,249 | A | | 5/1986 | Sunshine et al. | |
| 4,687,781 | A | * | 8/1987 | Ehrenpreis et al. | 514/557 |
| 4,839,176 | A | * | 6/1989 | Pankhania et al. | 424/465 |
| 5,500,227 | A | * | 3/1996 | Oshlack et al. | 424/476 |
| 2005/0281871 | A1 | * | 12/2005 | Petereit et al. | 424/451 |
| 2006/0127473 | A1 | * | 6/2006 | Nichols | 424/464 |

FOREIGN PATENT DOCUMENTS

| EP | 274845 A | | 7/1988 |
| ES | 2187566 T | | 6/2003 |
| WO | 9605834 | | 2/1996 |
| WO | WO 9915155 | * | 4/1999 |

OTHER PUBLICATIONS

Ansel (Pharmaceutical Dosage Forms and Drug Delivery Systems 1999, 7th Ed., Llippincott Williams & Wilkins; pp. 89-91, 196-197, 200, 201, 209-211, 213, 222 and 223).*

* cited by examiner

*Primary Examiner* — Ernst Arnold
(74) *Attorney, Agent, or Firm* — Tristan A. Fuierer; Andrew D. Gerschutz; Moore & Van Allen, PLLC

(57) ABSTRACT

The invention consists of a new formulation of ibuprofen and codeine in the form of a tablet, which comprises L-leucine in a concentration ranging between 4%-15% as a lubricant, in order to prevent the formulation mixture from adhering to the punches and to other elements of the compression machine during the compression process. The new formulation additionally comprises talc (0.5%-5.0%) and silicified microcrystalline cellulose (30%-80%). The formulation is preferably arranged in the form of a core that comprises the active principles and, amongst others, the L-leucine, part of the talc and the silicified microcrystalline cellulose; this core is coated with a composition that contains a copolymer of methacrylic acid and ethyl acrylate. The tablets of the invention do not exhibit flaking problems, have an adequate hardness with a convenient attrition to allow for subsequent coating, offer disintegration values of less than 5 minutes, with dissolution values for both active principles in accordance with those specified for rapid-release tablets.

13 Claims, 2 Drawing Sheets

PHARMACEUTICAL FORMULATION CONTAINING IBUPROFEN AND CODEINE

CROSS-REFERENCE TO RELATED APPLICATIONS

This application is filed under the provisions of 35 U.S.C. §371 and claims the priority of International Patent Application No. PCT/ES2008/070078 filed on 23 Apr. 2008 entitled "Improved Pharmaceutical Composition Containing Ibuprofen and Codeine" in the name of Maria Rosario Fernández de Gatta García, et al., which is hereby incorporated by reference herein in its entirety.

SCOPE OF THE INVENTION

This invention relates to improved pharmaceutical formulations that comprise ibuprofen and codeine (as the active substances), to the method of obtaining them and to their use in therapy. The technical field whereto they belong is the pharmaceutical field.

STATE OF THE ART

Ibuprofen belongs to the group of non-steroidal anti-inflammatory agents (NSAIs) derived from arylpropionic acid and has anti-inflammatory, analgesic and antipyretic activity. It is a racemic mixture of two enantiomers (S(+) and R(−)). Its chemical name is 2-(4-isobutyl-phenyl)propionic acid.

Ibuprofen is an active principle that requires relatively high dosages and the compression thereof is hindered by two facts: its bad fluidity characteristics and its low melting point.

Codeine is an opiaceous analgesic, with a lower potency than morphine and a lower addiction capacity; it is used as a cough suppressant and an anti-diarrhoeal and analgesic agent, in the latter case by itself or associated with NSAIs. Its chemical name is 7,8-didehydro-4,5-epoxy-3-methoxy-17-methyl-morphinan-6-ol.

The association of these two active substances is based on the fact that the sum of the analgesia obtained is greater than that of the individual components. Therefore, in the event of lack of analgesic response to an NSAI in mild to moderate pain, the WHO recommends combining a weak opioid such as codeine with an NSAI, in this case ibuprofen.

However, it has been found that pharmaceutical formulations which contain an association of ibuprofen and codeine present problems during storage. This is particularly observed in tablets, which, as time passes, lose colour and begin to disintegrate.

Tablets containing ibuprofen and codeine are disclosed, for example, in ES2187566. The stability problems exhibited by these tablets during storage, primarily due to the appearance of a yellow colouring and a tendency to disintegrate as time passes, are solved in said patent by the addition of a lubricant made from hydrogenated vegetable oil as an excipient.

A solution that has also been previously used to solve the same problem may be found in ES2035086. In said patent, the problems of loss of colour (yellowing of the tablet) and disintegration, when the tablet expands, cracks or fractures, with the consequent degradation of some of the components of the combination of active principles, either ibuprofen, codeine, or even both, are solved by adding insoluble carboxymethyl cellulose salts as an excipient.

Obviously, the solution to the above-mentioned storage problems should not undermine other parameters that make the formulation effectively applicable in therapy. We refer, for example, to the fact that the excipients used to improve stability during long-term storage of the tablets do not delay, for example, the availability of the active principles. In order to prevent potential negative effects on the availability of the tablets by any of the excipients selected to improve the stability of the tablets that contain ibuprofen and codeine during the storage thereof, EP0220805 proposes a biphasic pill, wherein each active principle is formulated separately in its respective phase, preferably adding microcrystalline cellulose as a lubricating compound that facilitates direct compression, in each of said phases corresponding to each active principle. In addition to ensuring stability of the tablets produced during the storage thereof, the production of these biphasic formulations does not damage the availability to patients who take them as a part of their treatment. However, this solution makes the manufacturing process of these tablets more complicated and expensive, since separate steps are necessary to form each phase of the final pill.

However, none of the solutions proposed in the state of the art, designed to optimise the stability of the tablets during the storage thereof, solves a problem that is inherent to the compression process itself; namely, the tendency of all the formulations that use lubricants such as those proposed in the state of the art—hydrogenated vegetable oil, insoluble carboxymethyl cellulose salts or microcrystalline cellulose, Lutrol Micro 68 or Lutrol Micro 127—to exhibit problems of adhesion to the punches, and even to the walls of the matrices, of the compression machine. This problem reduces the yield of the process of obtaining the tablets, since it damages the compression punches and affects other parts of the compression machine in an undesirable manner, and in some cases also causes flakes in the tablets produced (capping).

Moreover, the above-mentioned problem increases in the case of tablets composed of small particles of Ibuprofen when a high dose per tablet (400) is required, as opposed to the doses habitually used in the pharmacopeia (200). The advantage of manufacturing tablets with high doses of Ibuprofen is that this facilitates the dosage pattern, since, for example, only one tablet per day is needed, as compared to the 2 or 3 tablets required with the doses currently in existence in the market. Particularly in patients with memory problems, facilitating the prescription pattern is an additional advantage for a better treatment.

GENERAL DESCRIPTION OF THE INVENTION

Figure 1:
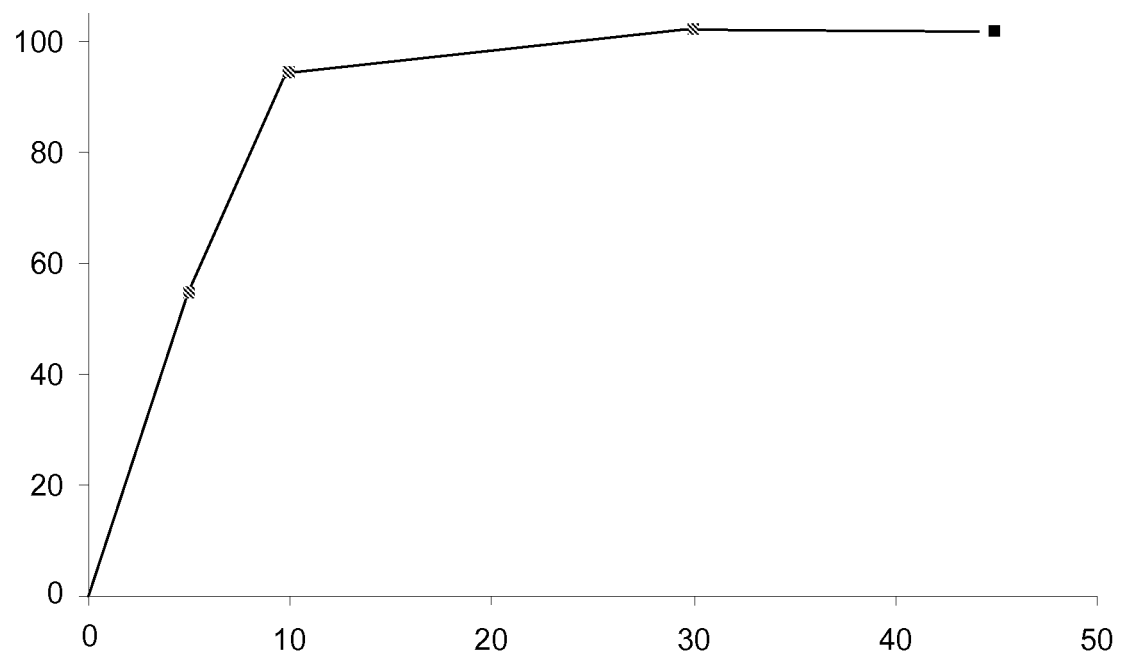
FIG. 1: Dissolution profile of Ibuprofen in the formulation proposed in Example 1.

In order to prevent the problem of "capping", without losing sight of the rest of the parameters that the formulation containing ibuprofen and codeine must meet, such as:
  Adequate tablet hardness
  Stability during storage (that it does not become yellow and does not disintegrate or become cemented)
  Degree of humidity of the tablet
  Dissolution rate of each active principle
  Tablet disintegration time
  No interaction between the active principles and the rest of the ingredients in the formulation In this invention, it was unexpectedly and surprisingly found that L-leucine, used as a lubricating excipient, prevented adhesion of the formulation to the components of the compression machine during formation of the tablets, without undermining the rest of the technical characteristics specified above, typical of formulations in the form of a tablet. The incorporation of L-leucine to the formulation of ibuprofen and codeine in tablets did not cause any yellowing or delay in the disintegration of the tablets during the long-term storage thereof, nor did it negatively affect the rest of the above-mentioned parameters of the formulation. Specifically, during storage under high-temperature and high-humidity conditions, no significant alterations took place in the dissolution of the active principles or in the disintegration of the tablets made with the formulation of the invention.

With the formulation of this invention, using L-Leucine as the lubricant, problems of insufficient lubrication are solved, there is greater stability in the disintegration of the tablets under high-temperature and humidity conditions, higher concentrations of lubricant may be used without affecting the release of the active principles and tablets with low disintegration times are obtained. Moreover, the formulations of the invention may be used with very small Ibuprofen particles, which are the most difficult to subject to direct compression. However, this invention is not limited to the direct compression method, whether in a single step or in more than one step, but may be applied with other methods, such as, for example, dry granulation.

Furthermore, the inclusion of silicified microcrystalline cellulose (SMCC) in the formulation of the invention improves the fluidity, produces tablets with a good weight uniformity (and, consequently, a good uniformity of the active principles), low attrition and low disintegration times. This is in contrast to the current extended use of non-silicified microcrystalline cellulose (MCC) in the State of the Art, which exhibits worse fluidity, a lower apparent density and produces tablets with a lower hardness.

Therefore, one object of this invention is to provide a stable preparation of the combination of Ibuprofen and codeine (preferably codeine phosphate hemihydrate) that resists the storage conditions of the tablets, in such a way that they do not lose colour, do not crack or expand, and maintain an in vitro level of disintegration and dissolution of the active principles that is in accordance with the specifications of the European Pharmacopeia, during the period of validity specified for the product. It has been observed that there is no degradation of the Ibuprofen or the codeine; therefore, the composition retains its therapeutic activity.

Another objective of this invention is to ensure that the process of obtaining the tablets takes place without any problems arising from lack of lubrication, and, therefore, that the formula does not adhere to the punches or the matrices of the compression machines.

DETAILED DESCRIPTION OF THE INVENTION

L-leucine was added to the formulation in the form of particles with a granulometry greater than 200 microns, for 90% of the particles added, and with a percentage of particles smaller than 50 microns less than or equal to 25%.

The Main Diluent/Ibuprofen ratio is of importance in this invention.

Specifically, Table I shows the dissolution of Ibuprofen in a formulation with a Diluent/Ibuprofen/Lubricant ratio of 0.5 and L-leucine as the lubricant; it shows 95% dissolution of Ibuprofen at 45 min, whereas, when using hydrogenated vegetable oil as the lubricant, for the same 0.5 ratio of the diluent with said active principle, the dissolution of Ibuprofen was only 67% at 45 min. The negative alteration of said parameters—decrease in the dissolution rate of each active principle and increase in the tablet disintegration time ("cementation")—is indicative of a decrease in the in vivo bioavailability of the active principles present in the formulation. In this invention, it has been surprisingly found that, for Diluent/Ibuprofen ratio values ≧0.5 and, preferably, ≧0.7, said cementation problems are prevented and, therefore, the bioavailability of Ibuprofen is ensured.

TABLE I

| PARAMETER | FORMULA Leucine T = 0 | FORMULA Leucine T = 4 wk at 40° C. and 75% RH | FORMULA Hydrog Veget Oil T = 0 | FORMULA Hydrog Veget Oil T = 4 wk at 40° C. and 75% RH |
|---|---|---|---|---|
| Hardness | 9.6 Kp | 11.4 Kp | 9.3 Kp | 12.2 Kp |
| Disintegration | 33" | 5'18" | 36" | 19'37" |
| Dissolution of Ibuprofen (% dissolved at 10, 20, 30 and 45 minutes) | 59, 84, 93, 93% | 41, 82, 94, 95% | 86, 99, 100, 101% | 15, 27, 43, 67% |
| Dissolution of Codeine (% dissolved at 10, 20, 30 and 45 minutes) | 101, 101, 100, 99% | 69, 100, 99, 98% | 101, 105, 103, 104% | 31, 43, 67, 94% |

RH: Relative Humidity in %

The concentration of L-leucine present in the formulation ranged between 4%-15%, preferably between 5%-10%. One of the preferred embodiments of the invention is that wherein 40 mg of L-leucine are added per tablet with an 800-mg core (without coating). This fact is significant, since other lubricants used in the formulations currently present in the state of the art, such as hydrogenated vegetable oils, at concentrations greater than 4%, produce lipid matrices that delay the availability of the active principle.

Table II shows that, in the case of the formulation of the invention, percentages of the L-Leucine lubricant of 10% or 15% do not affect the in vitro dissolution of Ibuprofen or of codeine after 45 min.

TABLE II

| FORMULA | ASSAYS | Results t = 0 | Results after 4 weeks at 40° C. and 75% RH |
|---|---|---|---|
| Formulation in accordance with Example 1 but with 10% L-Leucine | Hardness | 15.5 Kp | 17.3 Kp |
| | Disintegration | 6'57" | 15'09" |
| | Dissolution of Ibuprofen (% at 10, 20, 30 and 45 min) | 63, 89, 94, 94% | 36, 65, 91, 93% |
| | Dissolution of Codeine (% at 10, 20, 30 and 45 min) | 94, 100, 100, 99% | 36, 74, 99, 98% |
| Formulation in accordance with Example 1 but with 15% L-Leucine | Hardness | 15.1 Kp | 17.0 Kp |
| | Disintegration | 4'51" | 8'25" |
| | Dissolution of Ibuprofen (% at 10, 20, 30 and 45 min) | 70, 87, 94, 95% | 37, 82, 94, 95% |
| | Dissolution of Codeine (% at 10, 20, 30 and 45 min) | 99, 101, 101, 100% | 53, 91, 98, 98% |

Preferably, L-leucine was added in combination with talc as an anti-adhesion agent, in order to supplement the former's lubricating action. The percentage of talc present in the formulation ranged between 0.5% and 5%, preferably between 0.8%-2%. In one of the preferred embodiments of the invention, 10 mg of talc are added per tablet with an 800-mg core (without coating).

The presence of L-leucine in the formulation within the above-mentioned concentration ranges prevented adhesion of the mixture formulated to the parts of the tablet-forming machine. Moreover, the presence of L-leucine and talc, at the concentrations described, prevented yellowish colouring of the tablets during their storage and the cementation thereof (increase in the time required for disintegration after intake).

In order to better prevent cementation of the tablets, in addition to the presence of L-leucine and talc, a preferred embodiment of the invention also adds silicified microcrystalline cellulose to the formulation. In addition to preventing cementation of the tablet, the use of silicified microcrystalline cellulose as an additional excipient makes it possible for it to exhibit the following improved technical characteristics, as compared to the use of non-silicified microcrystalline cellulose:
a) Better mixing uniformities in direct compression processes.
b) Greater hardness and, consequently, more robust tablets, for the same compaction force.
c) Lower attrition and, therefore, better tablets for a subsequent coating process.
d) Lower percentages of disintegrants to obtain the same disintegration time.
e) Better compression for active principles with a low compactability, such as ibuprofen and codeine.

The silicified microcrystalline cellulose is added to the formulation in a percentage of 20%-80%, preferably 30%-50%. In one of the preferred embodiments of the invention, 295 mg of silicified microcrystalline cellulose are added for each tablet with an 800-mg core (without coating).

A significant aspect of this invention is the ratio between the silicified microcrystalline cellulose and ibuprofen. In a preferred embodiment of this invention, said ratio must be >0.7, which leads to a better dissolution of the active principles present in the formulation.

Specifically, for an ibuprofen/silicified crystalline cellulose ratio of 0.75, the dissolution of each active principle was >75% at 45 minutes of the dissolution assay, and no cementation of the tablet occurred under high-temperature (40° C.) and humidity conditions for 4 weeks.

A preferred embodiment of the invention is to start with a core of the formulation containing ibuprofen and codeine, and coat it with a 30% dispersion of a copolymer of methacrylic acid and ethyl acrylate (1:1). Specifically, having a coating around the core gives the formulation the following advantages:
a) Ibuprofen has a certain bitter taste and is quite pungent when taken directly in the form of uncoated tablets. One of the purposes of coating the tablets is to prevent these unpleasant sensations by applying a coating layer. This improves therapeutic compliance on the part of the patients.
b) To provide protection against humidity and light to the active principles contained in the core, thereby improving the product's stability profile, outside the packaging material.
c) To improve handling of the tablets in high-speed packaging machines by improving the tablets' mechanical stability through the coating process, without compromising the dissolution of the active principles.
d) Coating of the tablets facilitates their intake by patients (they are easier to swallow) and, thus, also improves therapeutic compliance.

Finally, the invention also comprises a method of manufacturing the formulation described above in the form of tablets, by both the dry granulation method and the direct compression method. The method basically comprises the following steps, performed in sequence:
1) Sieving of the Ibuprofen and the sodium starch glycolate through a 1,000-micron sieve.
2) Mixing of the previously sieved products, jointly with Codeine phosphate and silicified crystalline cellulose for 15 minutes.
3) Adding 100% of the talc and 60% of the L-leucine to the preceding mixture. Mix for 5 minutes.
4) Pre-compression and granulation of the tablets obtained through a mesh with a 1.6-mm opening.
5) Mixing of the granulate obtained with the remaining 40% of L-Leucine and mixing for 5 minutes.
6) Final obtainment of tablets with the preceding mixture in a rotary compression machine.
7) Coating of the Cores (uncoated tablets) by applying the aqueous coating suspension through spraying with an air gun.

The following examples, which are non-limiting, show a preferred quantitative and qualitative composition of the invention and the satisfactory assays measured regarding the tablets' stability parameters and the dissolution profile of the active principles, ibuprofen and codeine, contained in the formulation.

EXAMPLE 1

Core/Coating Formulation

| COMPONENT | Mg/tablet | Function | % Use |
|---|---|---|---|
| Ibuprofen | 400 | Active principle | 50% |
| Codeine phosphate hemihydrate | 30 | Active principle | 3.75% |
| Silicified microcrystalline cellulose | 295 | Diluent for Direct Compression | 36.9% with respect to total weight; 74% with respect to Ibuprofen |
| EXPLOTAB (sodium starch glycolate) | 25 | Disintegrant | 3.1% |
| L-Leucine | 40 | Lubricant | 5.0% |
| Talc | 10 | Lubricant | 1.25% |
| Total CORE | 800 mg | | |
| Coating | | | |
| EUDRAGIT L 30 D 55 (Poly(methacrylic acid, ethyl acrylate) 1:1) | 9.530 (2.859 dry residue) | Coating polymer | |
| Talc | 4.51 | Anti-adhesion agent | |
| Titanium dioxide | 2.86 | Opacifier | |
| Polyethylene glycol 6000 | 1.43 | Plasticiser | |
| Simethicone emulsion | 0.16 | Anti-foam agent | |
| Sodium carboxymethyl cellulose | 0.16 | Plasticiser | |
| Water | csp | Solvent | |
| Total COATED CORE | 812 mg | | |

EXAMPLE 2

Compatibility and Functionality Tests of the Selected Lubricants

In order to evaluate the degree of compatibility between L-leucine and the rest of the components of the formulation of Example 1, and, at the same time, determine the degree of lubrication provided, a mixture was prepared whereto L-leucine was added as the lubricant.

Tablets were obtained from the mixture assayed in accordance with the formulation of Example 1, evaluating the compression process, verifying whether or not the product became adhered to the punches and assessing the appearance of the tablets obtained and the compression process.

The tablets obtained which had the best functional behaviour were subjected to a Stability Study under accelerated conditions, and directly exposed on watch glasses for 4 weeks under conditions of 40° C. and 75% Relative Humidity, and, in parallel, 5° C.

The tablets were analysed every two weeks; and aspects such as hardness, humidity and disintegration time, which may be related to the dissolution of the active principles, were studied.

Below we describe the results of the compatibility study conducted for 4 weeks, in Table III.

The cores were compressed in an industrial rotary machine and, subsequently, the 10 kg of cores of each of the formulations were coated in a GS-10 drum, of the same brand as the industrial coating drum, under the following conditions:
Tablet load: 10 kg.
Inlet air temperature: 60° C.-70° C.
Outlet air temperature: 35° C.-45° C.
Temperature of the cores during the coating: 32° C.-36° C.
Quantity of impulse air: 7-8
Depression in the drum: sufficient
Spraying pressure: 1 kg/cm$^2$ The tablets thus obtained were used to start a pre-stability study in order to verify the physical and chemical stability of the formulation corresponding to Example 1, designed as follows:
Calendar: Sampling times: Beginning of the study and after 3, 6 and 9 months under the storage conditions:
   25° C. and 60% RH
   30° C. and 65% RH
   40° C. and 75% RH (at T=1 and 2 months, appearance, hardness and disintegration)
Packaging materials: Aluminum-PVDC blisters
Assays: Appearance, thickness, hardness, disintegration, humidity, dissolution, assessment and degradation products of the two active principles. (T=0 and T=3, 6 and 9 months)

TABLE III

| Storage Conditions | Appearance | Hardness (Kp) x | min | max | Thickness (mm) | Disinteg (s) | Humidity K-F (%) |
|---|---|---|---|---|---|---|---|
| T = 0 | C. White. w/o Coating | 13.1 | 12.0 | 14.3 | 6.22 | 36" | 2.03 |
| 5° C., 2 wk | C. White. w/o Coating | 10.7 | 8.6 | 11.7 | 6.17 | 16" | 2.90 |
| 5° C., 4 wk | C. White. w/o Coating | 11.4 | 10.1 | 12.1 | 6.36 | 24" | 2.87 |
| 40° C., 75% RH, 2 wk | C. White. w/o Coating | 13.4 | 12.6 | 14.3 | 6.21 | 1'49" | 2.86 |
| 40° C., 75% RH, 4 wk | C. White. w/o Coating | 13.6 | 12.9 | 14.3 | 6.41 | 3'16" | 2.75 |

In view of the results obtained, it was decided to continue to study the formulation with the new L-Leucine lubricant, at 5%, but, since the above-mentioned tests were performed at a laboratory scale in a small compression machine, it was decided to use a manufacturing mixture of about 10 kg with the selected mixture corresponding to the formulation of Example 1, in order to:
- Obtain more representative data of the industrial compression process.
- Have enough tablets to be coated in a GS-10 non-perforated drum (with automatic control of the air flow and extraction, and temperature of the air, the cores, the spray flow).
- Be able to estimate whether any type of interaction occurred between the formulation and the components of the coating suspension.
- Package the coated tablets in blisters and start a Stability Study in the final packaging material.

Table IV shows the results of said stability study. The detection and quantification limits must be taken into consideration when assessing the impurity content of the two active principles:
Impurity Content:
   n.d.=not detected-n.q.=not quantified.
Codeine Phosphate Hemihydrate:
   detection limit: <0.01%,
   quantification limit: <0.05%
Ibuprofen:
   detection limit: <0.01%,
   quantification limit: <0.05%
Appearance:
   COWT=coated oblong white tablet
Pre-Stability Results
   Conditions: 40° C. and 75% RH

TABLE IV

| Assay | Tentative specifications | T = 0 months | T = 1 month | T = 2 months | T = 3 months | T = 6 months |
|---|---|---|---|---|---|---|
| Appearance | COWT * | Complies | Slight Cream Col. | Cream colour | Dark cream colour | Dark cream colour |
| Humidity | 4.0% | 2.67% | | | 3.37% | 2.09 |

TABLE IV-continued

| Assay | Tentative specifications | T = 0 months | T = 1 month | T = 2 months | T = 3 months | T = 6 months |
|---|---|---|---|---|---|---|
| Hardness | Indicate (Kp) | 13.7 | 15.4 | 16.0 | 15.8 | 15.8 |
| Thickness | Indicate (mm) | 6.93 | 7.04 | 6.98 | 7.04 | 7.10 |
| Disintegration | 15 min. | 4' 00" | 5' 30" | 5' 49" | 9' 08" | 9' 28" |
| Dissolution (at 45 min.) | | | | | | |
| Codeine | ≧75% | 104.1% | | | 104.2% | 107.0% |
| Ibuprofen | ≧75% | 98.8% | | | 99.8% | 103.3% |
| Assessment | | | | | | |
| Codeine phosphate hemihydrate | 95.0%-105.0% | 98.3% | | | 99.5% | 99.0% |
| Ibuprofen | 95.0%-105.0% | 99.3% | | | 97.3% | 98.6% |
| Degradation products | | | | | | |
| From codeine phosphate hemihydrate: | 1.00% | 0.23% | | | 0.27% | 0.27% |
| Imp. A | 0.20% | n.q. | | | n.q. | n.q. |
| Imp. B | 0.20% | n.d. | | | n.d. | n.d. |
| Imp. C | 0.20% | n.d. | | | n.d. | n.d. |
| Imp. D | 0.20% | 0.09% | | | 0.07% | 0.08% |
| Imp. E | 0.10% | n.d. | | | n.q. | n.q. |
| Codeinone Other impurities (individual) | 0.10% | n.d. | | | n.d. | n.d. |
| Total impurities (Excep A) | 1.00% | 0.09% | | | 0.07% | 0.08% |
| Ibuprofen: | | | | | | |
| Imp. A | 0.30% | n.d. | | | n.d. | n.d. |
| Imp. B | 0.30% | n.d. | | | n.d. | n.d. |
| Imp. E | 0.30% | n.d. | | | n.d. | n.d. |
| Imp. J | 0.30% | n.d. | | | n.d. | n.d. |
| Imp. K | 0.30% | n.d. | | | n.d. | n.d. |
| Imp. L | 0.30% | n.d. | | | n.d. | n.d. |
| Imp. M | 0.30% | 0.1% | | | n.q. | n.d. % |
| Other impurities (individual) | 0.30% | n.d. | | | n.d. | n.d. |
| Total impurities | 1.00% | 0.10% | | | <0.05% | <0.05% |

Finally, an essential condition of the new formulation of this invention is to guarantee and maintain a dissolution profile of the selected formulation that ensures a correct in vitro dissolution of these tablets, so as to guarantee a correct release of the active principles, with a dissolution profile for both active principles that allows for their in vivo bioavailability.

To this end, the in vitro dissolution assay was performed, in an aqueous reservoir, for both active principles.

In order to select the conditions for the Dissolution Assay, the following factors were taken into consideration:

Solubility Characteristics of the Active Principles

Ibuprofen is practically insoluble in water and soluble in dilute alkaline solutions.

Codeine phosphate is soluble in water.

Since the tablets contain both active principles, the use of water as the medium for the dissolution assay was discarded, due to the insolubility of Ibuprofen therein. Moreover, since both active principles are absorbed in the gastro-intestinal tract, a buffer with a slightly alkaline pH seems to be indicated, that is, in accordance with those described in the pharmacopeia, phosphate buffer with pH 7.2.

Recommendations of the European Pharmacopeia for the dissolution assay, which specify that the volume of the dissolution medium must range between 500 and 1,000 ml, and the stirring speed must range between 50 and 100 rpm.

Taking the above points into consideration and, on the basis of the specifications of the US Pharmacopeia (USP 28) for the dissolution assay of Ibuprofen tablets (buffer, pH 7.2; 900 ml, blades, 50 rpm and 60 minutes as the assay time) and of codeine phosphate tablets (Water, 900 ml, blades, 50 rpm and 45 minutes as the assay time), the following conditions were tested in performing the dissolution assay:

Dissolution medium: phosphate buffer with pH 7.2.
Volume of the dissolution medium: 900 ml per cup
Device: blades
Stirring speed: 50 rpm
Final sampling time: 45 minutes
Moreover, additional samplings were performed at 5, 10 and 30 minutes in order to estimate the in vitro dissolution profile of the two active principles in the assayed formulation corresponding to Example 1.

Figure 2:
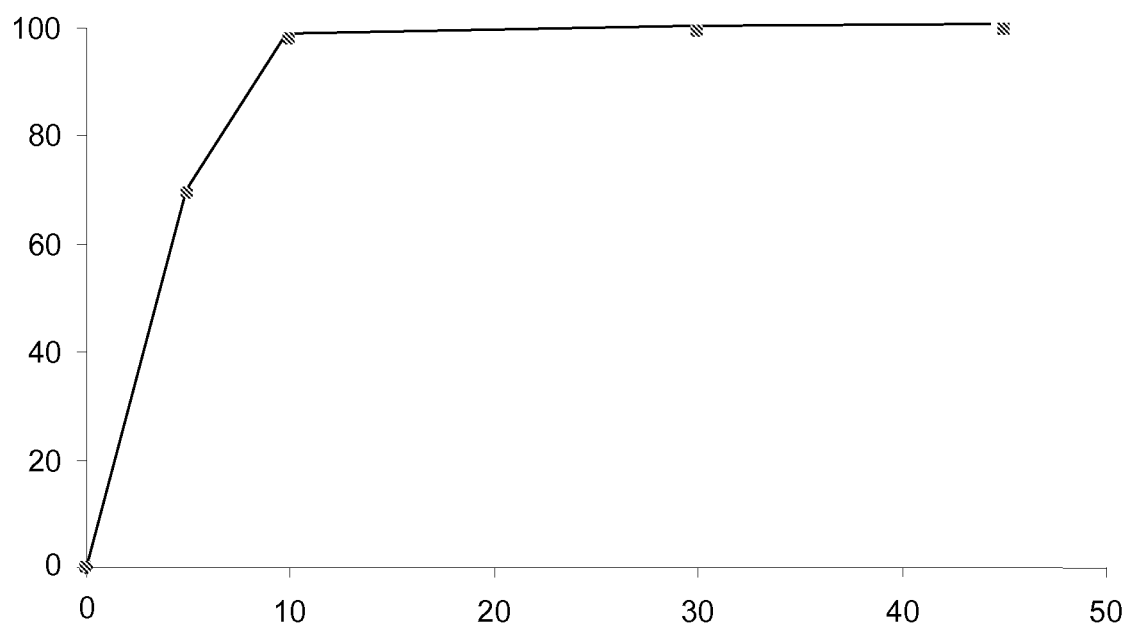
FIG. 2: Dissolution profile of Codeine phosphate hemihydrate in the formulation proposed in Example 1.

FIGS. 1 and 2 show, respectively, the results obtained for Ibuprofen and for Codeine with the dissolution assay described.

The results obtained in the tablets with the formulation corresponding to Example 1 were acceptable in terms of all the objectives proposed: the tablets were obtained without problems of adhesion to the different parts of the compression machine, without flaking problems, with a high hardness, with an adequate attrition to allow for a subsequent coating, with disintegration values of less than 15 minutes, with dissolution values for both active principles in accordance with the specifications of the Pharmacopeias in effect (≧75% of each active principle dissolved at 45 minutes).

The invention claimed is:

1. Formulation of a tablet that contains ibuprofen, and codeine, talc, sodium starch glycolate, and silicified microcrystalline cellulose, characterised in that it contains L-leucine in a concentration of between 4%-15% by weight of the tablet.

2. Formulation according to claim 1, wherein the concentration of L-leucine ranges between 5%-10% by weight of the tablet.

3. Formulation according to claim 1, wherein the concentration of talc is between 0.5%-5.0% by weight of the tablet.

4. Formulation according to claim 3, wherein the talc is present in a concentration range between 0.8%-2.0% by weight of the tablet.

5. Formulation according to claim 1, wherein the concentration of silicified microcrystalline cellulose is between 20%-80% by weight of the tablet.

6. Formulation according to claim 5, characterised in that the concentration range of silicified microcrystalline cellulose is between 30%-50%.

7. Formulation according to claim 5, wherein the ratio of silicified microcrystalline cellulose:ibuprofen is equal to or greater than 0.5.

8. Formulation according to claim 5, wherein the ratio of silicified microcrystalline cellulose:ibuprofen is equal to or greater than 0.7.

9. Formulation according to claim 1, characterised in that said formulation further comprises any other pharmaceutically acceptable excipient.

10. Formulation according to claim 1, characterised in that it comprises a core containing the following active principles: ibuprofen and codeine phosphate hemihydrate, jointly with the following excipients: L-leucine, talc, silicified microcrystalline cellulose and, sodium starch glycolate; and a coating of said core.

11. Formulation according to claim 10, characterised in that the composition of the core coating comprises a 30% dispersion of a copolymer having a 1:1 ratio of methacrylic acid to ethyl acrylate.

12. Formulation as claimed in claim 10, characterised in that the composition of the core coating additionally comprises a compound selected from the group consisting of: talc, titanium dioxide, polyethylene glycol, simethicone and/or sodium carboxymethyl cellulose, and combinations thereof.

13. A method of manufacturing the formulation of claim 1, characterised by the following steps operated in sequence:
  i.—Sieving of the Ibuprofen and sodium starch glycolate through a 1,000-micron sieve;
  ii.—Mixing of the previously sieved products, jointly with Codeine phosphate hemihydrate and silicified crystalline cellulose for 15 minutes;
  iii.—Adding 100% of the talc and 60% of the L-leucine to the preceding mixture and mixing for 5 minutes;
  iv.—Pre-compression and granulation of tablets obtained through a mesh with a 1.6-mm opening;
  v.—Mixing of granulate obtained with the remaining 40% of L-Leucine and mixing for 5 minutes;
  vi.—Final obtainment of tablets from the preceding mixture in a rotary compression machine; and
  vii.—Coating of the tablet cores from the preceding step by applying an aqueous coating suspension.

* * * * *